(12) United States Patent
Lilley

(10) Patent No.: US 11,769,390 B2
(45) Date of Patent: Sep. 26, 2023

(54) FURNITURE CLEANING MANAGEMENT SYSTEM

(71) Applicant: MILLERKNOLL, INC., Zeeland, MI (US)

(72) Inventor: Matthew James Lilley, Walker, MI (US)

(73) Assignee: MillerKnoll, Inc., Zeeland, MI (US)

( * ) Notice: Subject to any disclaimer, the term of this patent is extended or adjusted under 35 U.S.C. 154(b) by 192 days.

(21) Appl. No.: 17/342,020

(22) Filed: Jun. 8, 2021

(65) Prior Publication Data

US 2021/0383669 A1 Dec. 9, 2021

Related U.S. Application Data

(60) Provisional application No. 63/036,778, filed on Jun. 9, 2020.

(51) Int. Cl.
*G08B 21/18* (2006.01)
*G08B 21/22* (2006.01)
(Continued)

(52) U.S. Cl.
CPC .............. *G08B 21/182* (2013.01); *A61L 2/10* (2013.01); *A61L 2/24* (2013.01); *G01J 1/429* (2013.01);
(Continued)

(58) Field of Classification Search
CPC ......... G08B 21/182; G08B 21/22; A61L 2/10; A61L 2/24; A61L 2202/11;
(Continued)

(56) References Cited

U.S. PATENT DOCUMENTS 5,475,364 A 12/1995 Kenet
8,786,429 B2 7/2014 Li et al.
(Continued)

FOREIGN PATENT DOCUMENTS

CN 108634594 A 10/2018
JP 2002221443 A 8/2002
(Continued)

OTHER PUBLICATIONS

International Search Report with Written Opinion for related Application No. PCT/US2021/036400 dated Sep. 1, 2021 (15 Pages).

*Primary Examiner* — Ojiako K Nwugo
(74) *Attorney, Agent, or Firm* — MICHAEL BEST & FRIEDRICH LLP

(57) ABSTRACT

A furniture cleaning management system (FCMS) for a furniture affordance includes an indicator for indicating a state of the furniture affordance, a sensor option generating a signal indicating that the furniture affordance has been cleaned, and a processor receiving the trigger signal from the sensor option and causing the indicator to indicate that the furniture affordance is a cleaned state. The state of the furniture affordance indicated by the indicator may be selected from the cleaned state and a needs cleaning state. The processor may cause the indicator to indicate that the furniture affordance is in the needs cleaning state according to a schedule of furniture affordance occupancy, a schedule of furniture affordance cleaning, or as a consequence of sensing a user occupancy state at the furniture affordance.

18 Claims, 3 Drawing Sheets

(51) Int. Cl.
*G01P 13/00* (2006.01)
*A61L 2/24* (2006.01)
*A61L 2/10* (2006.01)
*G01J 1/42* (2006.01)
*G06V 40/20* (2022.01)

(52) U.S. Cl.
CPC .............. *G01P 13/00* (2013.01); *G06V 40/20* (2022.01); *G08B 21/22* (2013.01); *A61L 2202/11* (2013.01); *A61L 2202/14* (2013.01); *A61L 2202/17* (2013.01)

(58) Field of Classification Search
CPC .. A61L 2202/14; A61L 2202/17; G01J 1/429; G01P 13/00; G06V 40/20
See application file for complete search history.

(56) References Cited

U.S. PATENT DOCUMENTS

| | | | |
|---|---|---|---|
| 9,847,015 | B2 | 12/2017 | Li et al. |
| 9,922,533 | B2 * | 3/2018 | Hayes ................. A61L 2/26 |
| 10,004,823 | B2 | 6/2018 | Reid et al. |
| 10,479,328 | B2 | 11/2019 | Reibling et al. |
| 10,524,876 | B2 | 1/2020 | Schonfeld et al. |
| 10,560,811 | B2 | 2/2020 | Chen |
| 10,624,516 | B2 | 4/2020 | Cudzilo |
| 2009/0083114 | A1 | 3/2009 | Talarico |
| 2010/0319729 | A1 * | 12/2010 | Jensen ................. B08B 3/00 134/18 |
| 2011/0166826 | A1 | 7/2011 | Jensen et al. |
| 2011/0316695 | A1 * | 12/2011 | Li ................. G05D 1/0011 340/539.13 |
| 2012/0116803 | A1 | 5/2012 | Reid et al. |
| 2015/0220867 | A1 | 8/2015 | Christensen |
| 2016/0148485 | A1 * | 5/2016 | Hayes ................. A61L 2/26 340/665 |
| 2016/0179065 | A1 | 6/2016 | Shahabdeen |
| 2017/0068926 | A1 | 3/2017 | Eom et al. |
| 2017/0185930 | A1 | 6/2017 | Perry |
| 2018/0101826 | A1 | 4/2018 | Hultermans et al. |
| 2018/0158555 | A1 | 6/2018 | Cashman et al. |
| 2018/0249874 | A1 | 9/2018 | Kuhara |
| 2018/0252534 | A1 | 9/2018 | Kuhara |
| 2018/0280555 | A1 | 10/2018 | Bilenko et al. |
| 2018/0360558 | A1 | 12/2018 | Bassion, Sr. et al. |
| 2019/0251832 | A1 | 8/2019 | Longhenry et al. |
| 2019/0299259 | A1 | 10/2019 | Marra et al. |
| 2019/0354753 | A1 * | 11/2019 | Worrall ................. G06V 40/20 |
| 2021/0177218 | A1 * | 6/2021 | Jin ................. C11D 3/48 |

FOREIGN PATENT DOCUMENTS

| | | |
|---|---|---|
| JP | 2016106701 A | 6/2016 |
| KR | 2008000381 A | 1/2008 |
| KR | 2017030410 A | 3/2017 |
| WO | WO2009133527 A2 | 11/2009 |
| WO | WO2018142107 A1 | 9/2018 |

* cited by examiner

FURNITURE CLEANING MANAGEMENT SYSTEM

BACKGROUND

The present invention relates to a furniture cleaning management system. The system may include modules and processes for scheduled or identifying, confirming, and communicating that a furniture affordance should be cleaned and has been cleaned.

SUMMARY

The invention provides a furniture cleaning management system to assist in scheduling cleaning furniture affordances periodically or between uses to reduce the spread of germs between users of the furniture affordances.

In one aspect, the invention provides a furniture cleaning management system (FCMS) for a furniture affordance, the FCMS comprising: an indicator for indicating a cleaning status of the furniture affordance; a sensor option generating a trigger signal in response to sensing conditions that indicate a change in the cleaning status of the furniture affordance; and a processor receiving the trigger signal from the sensor option and causing the indicator to indicate the current cleaning status of the furniture affordance.

In another aspect, the furniture affordance includes a workstation. In another aspect, the indicator includes a clean indication for a clean status of the furniture affordance and a needs cleaning indication for a needs cleaning status of the furniture affordance. In another aspect, the sensor option includes an occupancy schedule for the furniture affordance and generates the trigger signal in response to the occupancy schedule indicating a change in occupancy of the furniture affordance. In another aspect, the sensor option includes a user occupancy sensor and generates the trigger signal in response to sensing a change in user occupying status for the furniture affordance. In another aspect, the sensor option includes an accelerometer generating the trigger signal in response to detecting a movement pattern of a portion of the furniture affordance associated with cleaning the portion of the furniture affordance. In another aspect, wherein the sensor option includes a UVC sensor generating the trigger signal in response to detecting exposure of a portion of the furniture affordance to a UV dose sufficient to inactivate a desired pathogen. In another aspect, the sensor option includes means for sensing cleaning products and generates the trigger signal in response to detecting cleaning products proximate a surface of the furniture affordance. In another aspect, the sensor option includes means for manually generating the trigger signal. In another aspect, the sensor option includes means for optically sensing a cleaning status of the furniture affordance and generating the trigger signal in response to optically sensing a change in cleaning status. In another aspect, the indicator includes an audible, visual, or tactile module generating an audible, visual, or tactile alert to indicate that the furniture affordance is in a cleaned state. In another aspect, the invention further comprises a communication circuit communicating between at least two of the indicator, sensor option, and processor; and a database for the cleaning status of the furniture affordance.

In another aspect, the invention provides a method for operating a furniture cleaning management system (FCMS) for a furniture affordance, the method comprising the steps of implementing via a processor: monitoring a sensor option to sense a cleaning status of the furniture affordance; generating a trigger signal in response to sensing, with the sensor, a change in cleaning status of the furniture affordance; generating a timestamp record in response to sensing the change in cleaning status; and causing an indicator to indicate the cleaning status of the furniture affordance in response to generating the trigger signal.

In another aspect, causing an indicator to indicate the cleaning status includes causing the indicator to indicate a clean status or a needs cleaning status. In another aspect, monitoring a sensor option includes monitoring an occupancy schedule for the furniture affordance and generating a trigger signal is performed in response to the occupancy schedule indicating a change in occupancy of the furniture affordance. In another aspect, monitoring a sensor option includes monitoring an occupancy sensor to detect a change in occupancy for the furniture affordance and generating a trigger signal is performed in response to detecting a change in user occupying status for the furniture affordance. In another aspect, monitoring a sensor option includes monitoring an accelerometer for movement of a portion of the furniture affordance consistent with cleaning and generating a trigger signal is performed in response to detecting movement consistent with cleaning. In another aspect, monitoring a sensor option includes monitoring a UVC sensor and generating a trigger signal is performed in response to detecting exposure of a portion of the furniture affordance to a UV dose sufficient to inactivate a desired pathogen. In another aspect, generating a trigger signal is performed by manual entry of the trigger signal. In another aspect, monitoring a sensor option includes monitoring an optical sensor and generating a trigger signal is performed in response to optically sensing a change in cleaning status.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
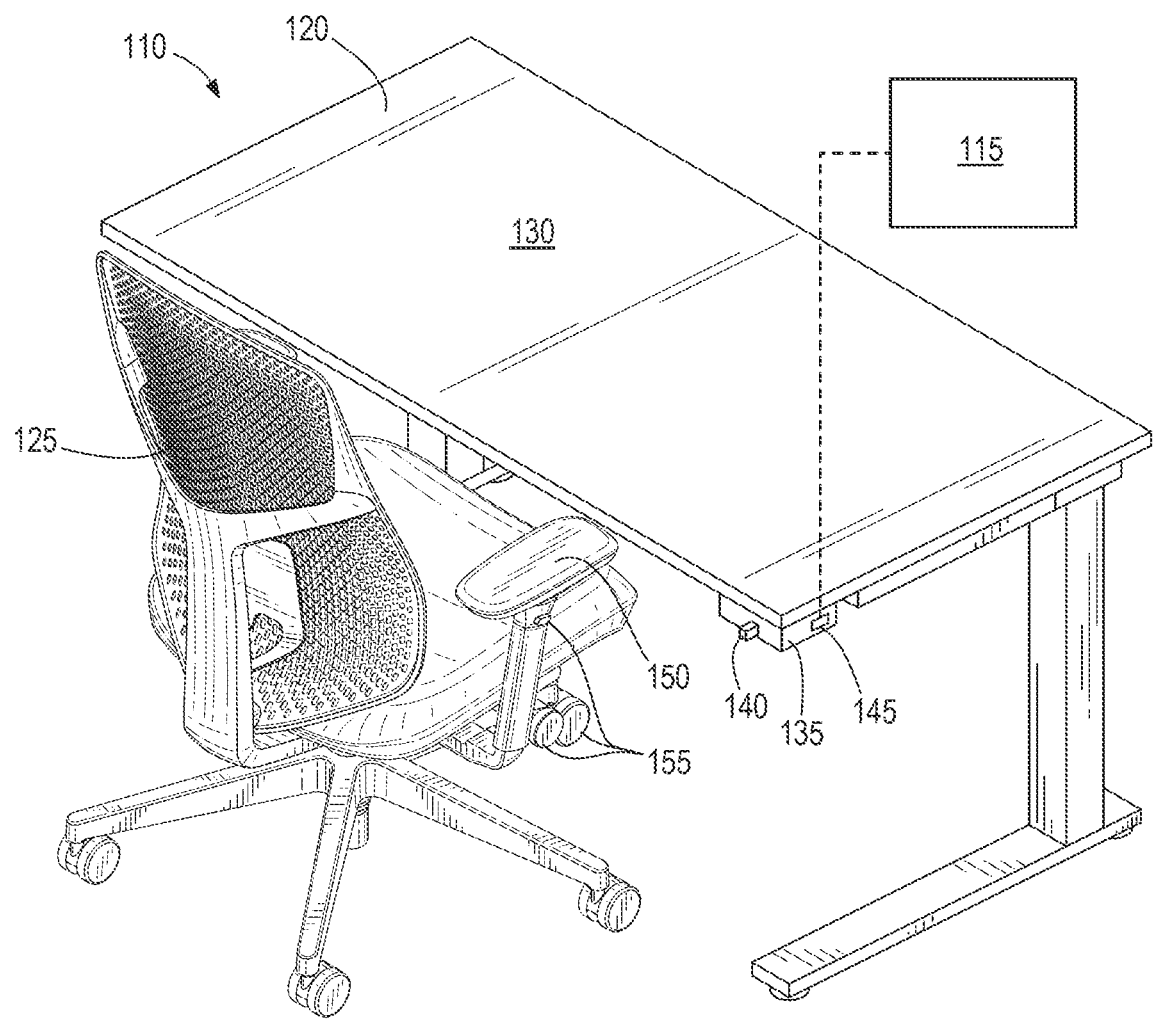
FIG. 1 is a schematic illustration of an exemplary embodiment of a furniture affordance including a furniture cleaning management system according the present invention.

FIG. 1 illustrates an exemplary embodiment of a furniture affordance 110 including or connected to a furniture cleaning management system ("FCMS") 115. The illustrated furniture affordance 110 is a workstation comprising a table 120 (e.g., a sit-stand table or desk) and a chair 125.

Figure 2:
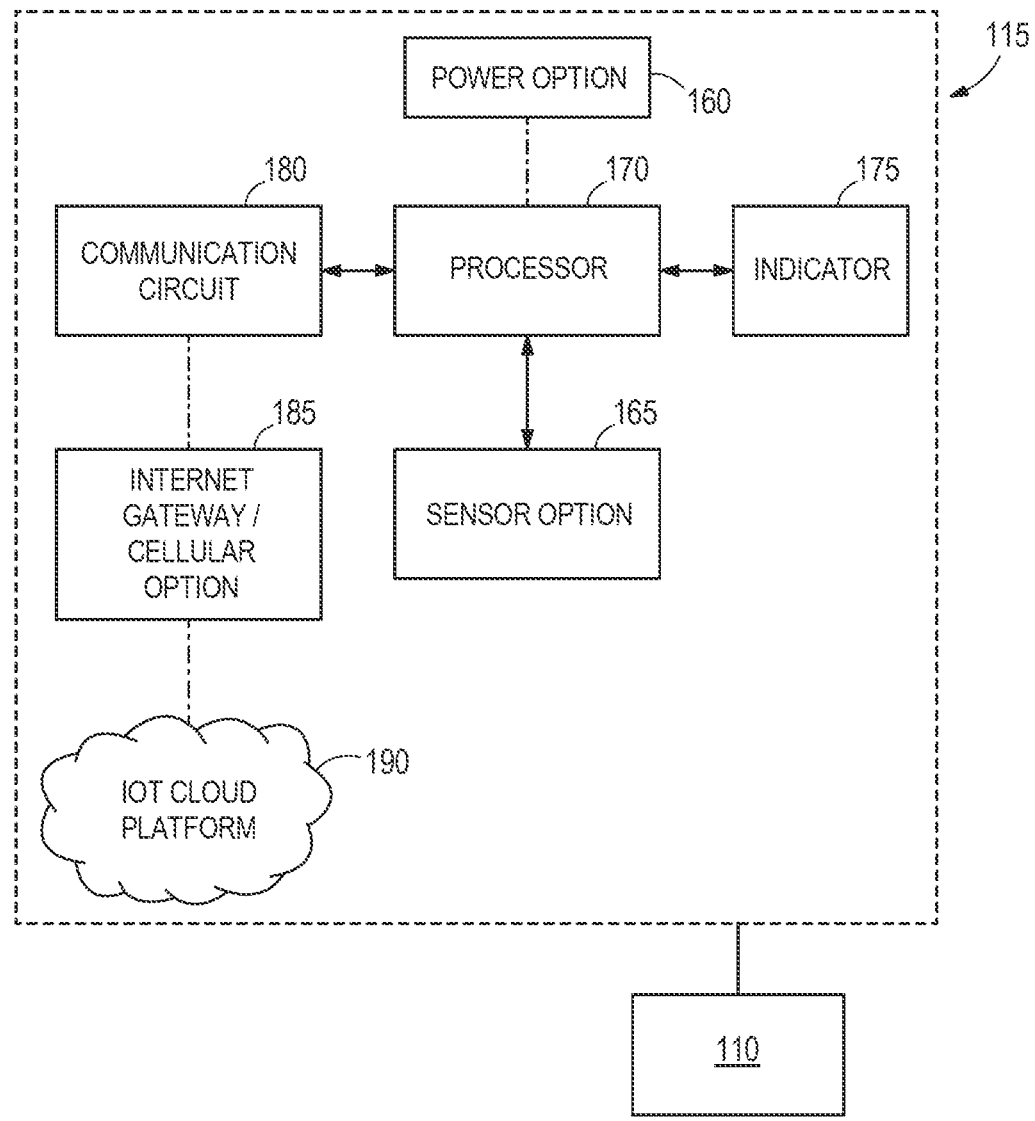
FIG. 2 is schematic illustration of the furniture cleaning management system.

FIG. 2 schematically illustrates a furniture affordance 110 including or connected to the FCMS 115. The term "furniture affordance" is used herein to broadly designate anything a user may sit on or come into contact with or any space a user may occupy. Without limiting the foregoing, furniture affordances include the workstation illustrated in FIG. 1, manufacturing equipment and other surfaces within manufacturing facilities, conference rooms and associated furniture and furnishings, televisions, lounge furniture, bookshelves, beds, lockers, sports and entertainment equipment, sanitary affordances such as toilets and sinks, and all furniture, surfaces, and spaces with which a user may come into contact in public and private environments. Such public and private environments, furniture, surfaces, and spaces include, for example and without limitation, manufacturing facilities, k-12 education facilities, lunch rooms, restaurants, hotels, rental vehicles (e.g., automobiles, bikes, boats), hospitals, dental and medical outpatient exam rooms, waiting rooms, houses of worship, arenas, homes, locker rooms, fitness facilities, golf courses, clubhouses, taxicabs, libraries, computer labs, experimental labs, office towers, airports, airplanes, salons, barber shops, rental centers, rental equipment, bowling alleys, miniature golf parks, theme parks, water parks, public recreation parks (e.g., benches), public restrooms, and zoos.

The furniture affordance 110 includes surfaces with which a user may come into contact, which may lead to the transfer and spread of germs. For example, the table 120 in FIG. 1 includes a tabletop 130, a height adjustment controller 135, including a control paddle 140, and an accelerometer 145 (which may be positioned in the controller 135 or elsewhere on the table 120). The accelerometer 145 is part of the FCMS 115 in the illustrated embodiment, even though it is illustrated separately from the FCMS 115. The chair 125 in FIG. 1 includes armrests 150 and chair setting controls 155. The tabletop 130, height adjustment controller 135, control paddle 140, armrests 150, and chair setting controls 155 are all considered contact surfaces in the context of this disclosure, although the definition is much broader as explained below.

The term "contact surface" refers to any surface of the furniture affordance with which a user can come into contact and which can carry and transmit germs to another user. In addition to the examples noted above, and without limiting the foregoing definition, contact surfaces may include handles, surfaces, shelves, headrests. The term "come into contact" includes physical contact with skin and clothing; breathing, sneezing, or coughing on; or any other interaction which could result in the transmission of germs. The term "germs" is used generically for viruses, bacteria, cysts, microorganisms, and any other transmissible pathogens that could infect or be further transmitted by a subsequent user of the furniture affordance.

FIG. 2 illustrates the FCMS 115 in combination with a generic furniture affordance 110. Depending on the configuration of the FCMS 115, it may include some or all of: a power option 160; a sensor option 165; a processor 170; an indicator 175; a communication circuit 180; an internet gateway or cellular module 185, and an IOT cloud platform 190.

The power option 160 may comprise: an on-board powered device; a power cord; a wall socket; an AC adapter; a battery or bank of batteries; a relocatable power tap (RPT) (e.g., the product sold under the name Logic by Herman Miller, Inc.); a USB charger (UBI); a task light nearby the furniture affordance; solar cells; fuel cells; an internal combustion engine (e.g., in an automobile or outdoor power equipment); or any other source from which the furniture affordance 110 receives or derives power. In FIG. 1, the power option 160 takes the form of the height adjustment controller 135 which receives power from a wall socket or other power conduit in the building and room in which the table 120 is situated.

As will become apparent below, this disclosure uses terms such as "signal" and "trigger" in multiple scenarios. These are intended to be broad terms and are largely overlapping in meaning. Indeed, in some instances the term "trigger signal" is used to indicate that the signal is also a trigger to set off some other act or process. For example, the sensor option 165 can generate a signal that is conveyed across the communication circuit 180 to the processor 170 and the processor 170 may interpret the signal as a trigger to take some action or the signal may be said to trigger the processor 170 into some action (e.g., create a "clean" or "needs cleaning" timestamp in a database). In this sense the sensor option 165 signal can also be called the trigger because, in this example, the signal will always cause the processor 170 to generate the trigger. Triggers (and by association the signals that may cause the triggers) are referred to as "clean triggers" and "needs cleaning triggers" throughout this disclosure to reference triggers associated with a furniture affordance being found or judged clean or not clean, respectively. When used on its own, the term "trigger" can mean a change of status between clean and needs cleaning. The terms "clean" and "needs cleaning" are collectively referred to as the cleaning state or cleaning status of the furniture affordance.

The term sensor option 165 includes traditional sensors which react to an input by generating a signal and schedulers and timers which do not take an input but do generate an output in the form of an indication that a cleaning of the contact surface should occur or is scheduled to occur. The sensor option 165 could alternatively include a UVC sensor capable of detecting exposure to a germicidal lamp and detecting a predetermined intensity of UV light, such as 40 mJ of UV or another dose sufficient to inactivate surface germs. Alternatively, the sensor option 165 could include a sensor specifically able to detect ozone concentration proximate the contact service and at sufficient levels and time to provide a localized disinfecting affect. Also, the sensor option 165 could include a sensor to detect a specific cleaner i.e. ammonia or alcohol base on or near (i.e., proximate) the contact surface. The term "cleaning products" is used to include any cleaning products including those described above. The sensor option 165 can therefore be referred to as a means for sensing cleaning products when it is a type that generates the trigger signal in response to sensing cleaning products. In this regard, the term sensor option 165 means any device, subsystem, or schedule by which the FCMS detects, determines, or deduces that the contact surface has been cleaned.

In FIG. 1, the sensor option 165 comprises the accelerometer 145, which can detect the distinct movement patterns associated with cleaning the tabletop 130. The sensor option 165 in the illustrated embodiment may also include logic in the FCMS 115 which deduces that the other contact surfaces 135, 140, 150, 155 have been cleaned when the tabletop 130 has been cleaned. This and other examples of sensor options 165 are described below.

Specific examples of suitable sensor options 165 include, without limitation: an accelerometer (e.g., accelerometer 145) that can detect cleaning\wiping movement based on algorithm; a VOC or environmental sensor that can detect spray or environmental change in air (e.g., in a conference room or other space based implementation); a mobile device having a Bluetooth® direct connection with the furniture affordance and running a mobile app such that the trigger signal is generated by the mobile device in response to a user manually entering a cleaned status for the furniture affordance via the app and the trigger signal directly resets the furniture affordance indicator to a cleaned state; a cloud based device that uses a cloud based connection with a mobile device, the cloud based device generating the trigger signal in response to a cleaned status for the furniture affordance being manually entered on the mobile device; a time based sensor generating the trigger signal in response to the elapsing of a predetermined time (e.g., some period of hours) associated with a cleaning schedule; an accelerometer (e.g., accelerometer 145) that detects a reset code (e.g., a knock sequence such as the familiar shave-and-a-haircut pattern) being tapped against a surface of the furniture affordance in the vertical (Z-axis) detection; a furniture height sensor for adjustable-height furniture which senses that the furniture affordance height has been moved to a predetermined height (e.g., full-up or full-down) to indicate the furniture affordance has been cleaned; an RFID badge and an RFID proximity sensor, one of which is worn or carried by the cleaning personnel and the other of which is on the furniture affordance, the RFID proximity sensor generating the trigger signal in response to detecting the RFID badge and resetting the furniture affordance to the cleaned state when detected; an RFID tag using close proximity detection (e.g., 128 Khz low frequency or 13.56 Mhz RFID including near field communication or equivalent range); an optical or camera recognition to sense a QR code or optical code that indicates a cleaner has reset the system; a Bluetooth® or RF beacon worn by a cleaner and resetting the furniture affordance to the cleaned state when in proximity for a given time; a Bluetooth® or RF beacon mounted to or near the furniture affordance, which is read by a cleaner's phone or PC app and auto resets the furniture affordance to the cleaned state via the cloud or Bluetooth®; a PIR (passive infrared) sensor that detects occupancy of the furniture affordance for a predetermined period; a button or combination of buttons which can be pressed or used to enter a press code; a biometric screener that uses a fingerprint or other biometric scan to determine that a cleaner has been present; a pressure sensor to detect the weight of a user in proximity to the furniture affordance; or a thermal imaging device that detects motion of an object with temperature conducive to a human with normal temperature in proximity to the furniture affordance for a specified duration. Bluetooth®, RF, PIR, nearfield, and any other form of wireless communication are referred to herein collectively as wireless communication. Camera, QR codes, and other optical codes are collectively referred to as optical codes and the sensors for such optical codes is referred to as means for optically sensing a cleaning status. Entry of a cleaning status via a mobile app or by pressing a button or buttons on the furniture affordance or by tapping a sequence on the furniture affordance or by any other means in which the user actively indicates that the cleaning status has changed are referred to collectively as "manual entry" of the trigger and the mode of entering the manual entry is referred to as means for manually generating the trigger signal.

The illustrated processor 170 may be a standard MCU, ASIC, FPGA, or alternatively a remotely hosted processing device.

The illustrated indicator 175 in FIG. 1 comprises the control paddle 140 which is part of the height adjustment controller 135. The controller paddle 140 may include, for example, LEDs which can cause the control paddle 140 to illuminate in multiple colors to indicate that the furniture affordance is in a cleaned state. Alternatively, a multi-color LED can be provided elsewhere on the table 120 and connected to the processor 170. Alternatively, the indicator 175 can include a mobile device in wireless communication with the processor or could be an audible, visual, or tactile (e.g., vibration) module in wireless communication with the processor, the mobile device or module being controllable by the processor to indicate that the furniture affordance is in a cleaned state. The indicator 175 could simply be a menu of available furniture affordances—if a furniture affordance appears on the menu, it is clean and available. Alternatively, the indicator may be an icon next to furniture affordances on a list (e.g., on a mobile device app) with icons for in use, vacant, clean and needs cleaning. The indicator 175 is operated by the processor 170 to indicate a state or status of the furniture affordance 110. The state or status indicated by the indicator 175 may include a "cleaned" state or status and a "needs cleaning" state or status. The terms "state" and "status" are used interchangeably. The state of the furniture affordance 110 may be a function of an occupancy schedule of the furniture affordance 110 or a cleaning schedule for the furniture affordance 110, or may be derived from sensing an actual occupancy state or status (e.g., occupied or not occupied) of the furniture affordance 110.

Although illustrated in FIG. 1 as LEDs in the control paddle 140 of the height adjustment controller, in other embodiments the indicator may comprise a stand-alone light (e.g., an LED) or any other means for indicating to a user the cleaning status of the furniture affordance 110. For example, a light may be illuminated in one color when the furniture affordance 110 requires cleaning or is scheduled for routine cleaning, and may be illuminated in another color after the contact surfaces of the furniture affordance 110 have been cleaned. The indicator 175 may in other embodiments be a text message or other notification (e.g., via an app) to the mobile device of a user waiting for the furniture affordance. In other embodiments, the indicator 175 may be the inclusion or exclusion of the furniture affordance 110 on a list of available furniture affordances (e.g., on a mobile device app), it being understood that inclusion of a furniture affordance 110 on the list indicates that it has been cleaned and exclusion of a furniture affordance 110 on the list indicates that it has not been cleaned. Alternatively a mobile app may include a list of cleaned and uncleaned furniture affordances 110 or have icons next to furniture affordances 110 on a list to indicate whether the furniture affordances 110 have been cleaned.

The communication circuit 180 communicates between at least two of the indicator, sensor option, and processor. The communication circuit 180 may comprise an antenna, RF transceiver and peripherals in the case of wireless communication, alternatively this circuit could comprise a hard-wired data transceiver circuit including but not limited to LIN, UART, USB, Ethernet, fiber optic or other physical connection data protocol. The communication circuit sends a status signal to a database to indicate whether a particular furniture affordance has been cleaned (i.e., is in the cleaned state). The communication circuit 180 may also send information from the database to the processor 170 to change the status of a furniture affordance 110 based on the occupancy schedule of the furniture affordance 110 or the cleaning schedule of a cleaning staff.

The illustrated internet gateway or cellular module 185 comprises an RF transceiver or physical data protocol connection matching that of the sensors (e.g., ANT wireless, BLE, ZigBee or other). The gateway or cellular module 185 interfaces with the Internet via wire or wireless communication or with a cellular data system.

The illustrated IOT cloud platform 190 comprises data storage and remote data processing capabilities hosted on a remotely connected network or system. The IOT cloud platform 190 sends and receives information to and from the internet gateway/cellular module 185 to place mobile device apps in communication with the processor 170.

Figure 3:
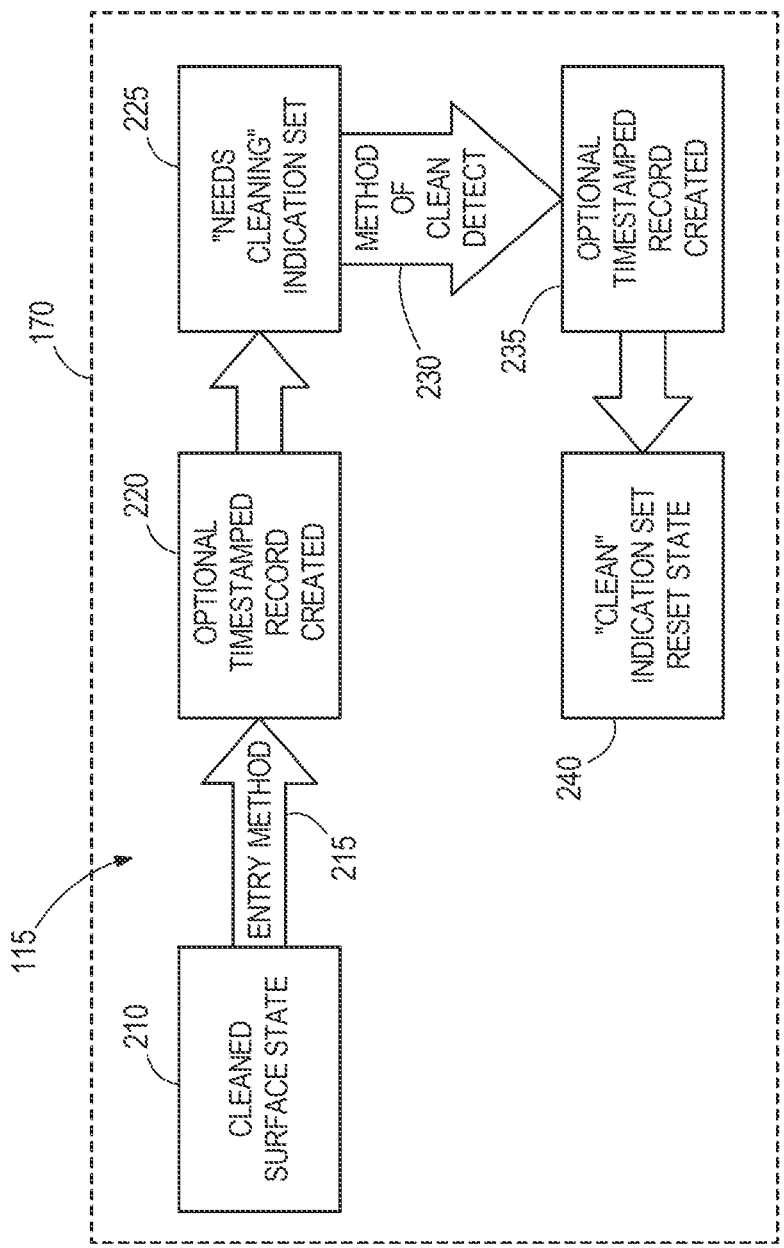
FIG. 3 a flow chart for the furniture cleaning management system.

FIG. 3 is a flow chart for the FCMS 115, which is programmed in the processor 170. The logic starts at 210, with a status of "clean" for the contact surfaces 135. As used herein, the term "clean" means that germs on contact surfaces are removed or rendered inactive. The FCMS 115 designates the contact surfaces as being in a clean stated when the FCMS 115 deems them clean. The clean status may be initiated via a keyboard or mobile device, for example, and may be manual or automatic. The clean status is received by the processor 170 at 215 in the flow chart. In the illustrated embodiment of FIG. 1, the processor 170 illuminates the LEDs in the control paddle 140 in a first color (e.g., green) to indicate that the contact surfaces 130, 135, 140, 150, 155 are clean. The processor 170 also creates a time-stamped record at 220 to record the date and time when the contact surfaces were designated as clean.

The indicator 175 remains in the clean status until a needs cleaning triggering event which indicates that the contact surfaces need cleaning at 225. The needs cleaning triggering event may be, for example, a user reserves or checks-in to an available owned furniture affordance 110 BLE or Cloud and checks out or reservation expired. Another example of a needs cleaning triggering event is the sensor option 165 detects occupancy for a set period. The sensor option 165 may include an environmental sensor that detects an increase in CO2 caused by occupancy in an enclosed space (which may be the furniture affordance 110 in that application), and the detection of a certain concentration of CO2 could be the needs cleaning triggering event. The needs cleaning triggering event might alternatively be an external scheduling module which determines that the contact surfaces need cleaning based on a user being scheduled to use the furniture affordance 110. The needs cleaning triggering event can be just before or just after occupancy of the furniture affordance 110. The needs cleaning triggering event may be time based, in which the furniture affordance 110 receives regularly-schedule cleanings at certain intervals (e.g., every 2 hours, 4 hours, 6 hours, or 12 hours). If the sensor option 165 includes the functionality to measure temperatures in the vicinity of the furniture affordance 110, the needs cleaning triggering event may be the detection of a human fever thermal profile in proximity to the area or a surface of the furniture affordance 110. In the illustrated embodiment of FIG. 1, when the needs cleaning triggering event occurs, the processor 170 changes the color of control paddle 140 illumination to a second color (e.g., red) while the workstation is in the "needs cleaning" state.

At 230, the processor, working through the sensor option 165, determines that the contact surfaces are being cleaned, are cleaned, or should be clean. The processor or sensor option 165 generates a clean trigger in response to sensing or determining that the contact surfaces are being cleaned. In the illustrated embodiment of FIG. 1, the method for detecting that the contact surfaces are being cleaned comprises monitoring the accelerometer 145 for a signal that the cleaning is being conducted or is complete. For example, the accelerometer 145 may detect a sequence of taps on the desktop made by the cleaning staff to indicate that the cleaning is complete. In another example, the accelerometer 145 may detect a pattern of vibrations consistent with cleaning the tabletop 130, such as repeated rubbing motions over the tabletop 130 coupled with a downward, z-axis force applied to the tabletop 130. The signals from the accelerometer 145 may be interpreted by the processor 170 to conclude that cleaning being conducted. The processor 170 may further deduce that all other contact surfaces 135, 140, 150, 155 in the workstation that are not monitored via the accelerometer 145 are also cleaned at the same time as the tabletop 130. Alternatively, accelerometers may be provided on all furniture affordances 110 to sense cleaning of all contact surfaces.

Turning to step 235 of FIG. 3, once the processor 170 has determined that the contact surfaces have been cleaned, it may optionally generate a time-stamped record to record the cleaning. The "clean" indication (e.g., illuminate the paddle 140 green again in the illustrated embodiment of FIG. 1) is then enacted by the processor 170 and the indicator at step 240, and the process starts again.

Thus, the invention provides, among other things a furniture cleaning management system that includes modules and processes for scheduled or identifying, confirming, and communicating that a furniture affordance should be cleaned and has been cleaned. Various features and advantages of the invention are set forth in the following claims.

What is claimed is:

1. A furniture cleaning management system (FCMS) for a furniture affordance, the FCMS comprising:
 an indicator for indicating a cleaning status of the furniture affordance;
 a sensor option generating a trigger signal in response to sensing conditions that indicate a change in the cleaning status of the furniture affordance; and
 a processor receiving the trigger signal from the sensor option and causing the indicator to indicate the current cleaning status of the furniture affordance;
 wherein the sensor option includes a user occupancy sensor and generates the trigger signal in response to sensing a change in user occupying status for the furniture affordance.

2. The FCMS of claim 1, wherein the furniture affordance includes a workstation.

3. The FCMS of claim 1, wherein the indicator includes a clean indication for a clean status of the furniture affordance and a needs cleaning indication for a needs cleaning status of the furniture affordance.

4. The FCMS of claim 1, wherein the sensor option includes an occupancy schedule for the furniture affordance and generates the trigger signal in response to the occupancy schedule indicating a change in occupancy of the furniture affordance.

5. A furniture cleaning management system (FCMS) for a furniture affordance, the FCMS comprising:
 an indicator for indicating a cleaning status of the furniture affordance;
 a sensor option generating a trigger signal in response to sensing conditions that indicate a change in the cleaning status of the furniture affordance; and
 a processor receiving the trigger signal from the sensor option and causing the indicator to indicate the current cleaning status of the furniture affordance;
 wherein the sensor option includes an accelerometer generating the trigger signal in response to detecting a movement pattern of a portion of the furniture affordance associated with cleaning the portion of the furniture affordance.

6. The FCMS of claim 1, wherein the sensor option includes a UVC sensor generating the trigger signal in response to detecting exposure of a portion of the furniture affordance to a UV dose sufficient to inactivate a desired pathogen.

7. The FCMS of claim 1, A furniture cleaning management system (FCMS) for a furniture affordance, the FCMS comprising:
an indicator for indicating a cleaning status of the furniture affordance;
a sensor option generating a trigger signal in response to sensing conditions that indicate a change in the cleaning status of the furniture affordance; and
a processor receiving the trigger signal from the sensor option and causing the indicator to indicate the current cleaning status of the furniture affordance;
wherein the sensor option includes means for sensing cleaning products and generates the trigger signal in response to detecting cleaning products proximate a surface of the furniture affordance.

8. The FCMS of claim 1, wherein the sensor option includes means for manually generating the trigger signal.

9. The FCMS of claim 1, wherein the sensor option includes means for optically sensing a cleaning status of the furniture affordance and generating the trigger signal in response to optically sensing a change in cleaning status.

10. The FCMS of claim 1, wherein the indicator includes an audible, visual, or tactile module generating an audible, visual, or tactile alert to indicate that the furniture affordance is in a cleaned state.

11. The FCMS of claim 1, further comprising a communication circuit communicating between at least two of the indicator, sensor option, and processor; and a database for the cleaning status of the furniture affordance.

12. A method for operating a furniture cleaning management system (FCMS) for a furniture affordance, the method comprising the steps of implementing via a processor:
monitoring a sensor option to sense a cleaning status of the furniture affordance;
generating a trigger signal in response to sensing, with the sensor, a change in cleaning status of the furniture affordance;
generating a timestamp record in response to sensing the change in cleaning status; and
causing an indicator to indicate the cleaning status of the furniture affordance in response to generating the trigger signal;
wherein monitoring a sensor option includes monitoring an occupancy sensor to detect a change in occupancy for the furniture affordance and generating a trigger signal is performed in response to detecting a change in user occupying status for the furniture affordance.

13. The method of claim 12, wherein causing an indicator to indicate the cleaning status includes causing the indicator to indicate a clean status or a needs cleaning status.

14. The method of claim 12, wherein monitoring a sensor option includes monitoring an occupancy schedule for the furniture affordance and generating a trigger signal is performed in response to the occupancy schedule indicating a change in occupancy of the furniture affordance.

15. A method for operating a furniture cleaning management system (FCMS) for a furniture affordance, the method comprising the steps of implementing via a processor:
monitoring a sensor option to sense a cleaning status of the furniture affordance;
generating a trigger signal in response to sensing, with the sensor, a change in cleaning status of the furniture affordance;
generating a timestamp record in response to sensing the change in cleaning status; and
causing an indicator to indicate the cleaning status of the furniture affordance in response to generating the trigger signal;
wherein monitoring a sensor option includes monitoring an accelerometer for movement of a portion of the furniture affordance consistent with cleaning and generating a trigger signal is performed in response to detecting movement consistent with cleaning.

16. The method of claim 12, wherein monitoring a sensor option includes monitoring a sensor that is capable of detecting a predetermined intensity of UV light and generating a trigger signal is performed in response to detecting exposure of a portion of the furniture affordance to a UV dose sufficient to inactivate a desired pathogen.

17. The method of claim 12, wherein generating a trigger signal is performed by manual entry of the trigger signal.

18. The method of claim 12, wherein monitoring a sensor option includes monitoring an optical sensor and generating a trigger signal is performed in response to optically sensing a change in cleaning status.

* * * * *